US00PP19790P2

(12) United States Plant Patent
Danziger

(10) Patent No.: US PP19,790 P2
(45) Date of Patent: Mar. 3, 2009

(54) ***LOBELIA* PLANT NAMED 'DANANB6'**

(50) Latin Name: *Lobelia erinus*
Varietal Denomination: DANANB6

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,647

(22) Filed: Jan. 11, 2008

(51) Int. Cl.
*A01H 5/00* (2006.01)

(52) U.S. Cl. ..... Plt./451

(58) Field of Classification Search ..... Plt./263, Plt./451

See application file for complete search history.

*Primary Examiner*—Annette H Para
*Assistant Examiner*—S. B. McCormick Ewoldt

(57) ABSTRACT

A new and distinct *Lobelia* cultivar named 'DANANB6' is disclosed, characterized by having bright blue flowers flowers, trailing plant habit, highly floriferous flowering and neutral flowering habit. The new variety is a *Lobelia,* normally produced as an outdoor garden or container plant.

2 Drawing Sheets

Latin name of the genus and species: *Lobelia erinus.*
Variety denomination: 'DANANB6'.

BACKGROUND OF THE INVENTION

The new *Lobelia* cultivar is a product of a planned breeding program conducted by the inventor, Gabriel Danziger, in Moshav Mishmar Hashiva, Israel. The objective of the breeding program was to produce new trailing perennial *Lobelia* varieties. The seed parent is the unpatented, proprietary seedling variety referred to as *Lobelia erinus* 'LOB-6-382.' The pollen parent is the unpatented, proprietary seedling variety referred to as *Lobelia erinus* 'LOB-6-241.' The new variety was discovered in April 2005 by the inventor in a group of seedlings resulting from that crossing, in a commercial greenhouse in Moshav Mishmar Hashiva, Israel.

Asexual reproduction of the new cultivar 'DANANB6' by vegetative cuttings was first performed at a commercial greenhouse in Moshav Mishmar Hashiva, Israel in April 2005. Subsequent propagation has shown that the unique features of this cultivar are stable and reproduced true to type on successive generations.

SUMMARY OF THE INVENTION

The cultivar 'DANANB6' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANANB6' These characteristics in combination distinguish 'DANANB6' as a new and distinct *Lobelia* cultivar:

1. Trailing plant habit.
2. Large flowers.
3. Flat flower, whereas most *Lobelias* have undulating flowers.

Plants of the new cultivar 'DANANB6' are similar to plants of the parent, *Lobelia erinus* 'LOB-6-382' in most horticultural characteristics, however, plants of the new cultivar 'DANANB6' are trailing, compared to an erect habit of the female parent. Additionally, plants of the new variety have glossy green leaves, compared to matte leaves of the female parent, and flowers of the new variety are blue with a white eye, compared to all blue of the female parent.

Plants of the new cultivar 'DANANB6' are similar to plants of the parent, *Lobelia erinus* 'LOB-6-241' in most horticultural characteristics, however, plants of the new cultivar 'DANANB6' are trailing, compared to the mounded habit of the pollen parent. Additionally, plants of the new variety have a lighter blue flower than the male parent.

COMMERCIAL COMPARISON

Plants of the new cultivar 'DANANB6' are best compared to the commercial variety 'WESLOSPOT,' U.S. Plant Pat. No. 15,835. The new variety 'DANANB6' is similar to 'WESLOSPOT' in most horticultural characteristics, however, 'DANANB6' plants have a trailing habit compared to the erect habit of 'WESLOSPOT.' Additionally, plants of 'DANANB6' have thinner, more flexible branches, and much glossier leaves than plants of 'WESLOSPOT.'

BRIEF DESCRIPTION OF THE PHOTOGRAPH

Figure 1:
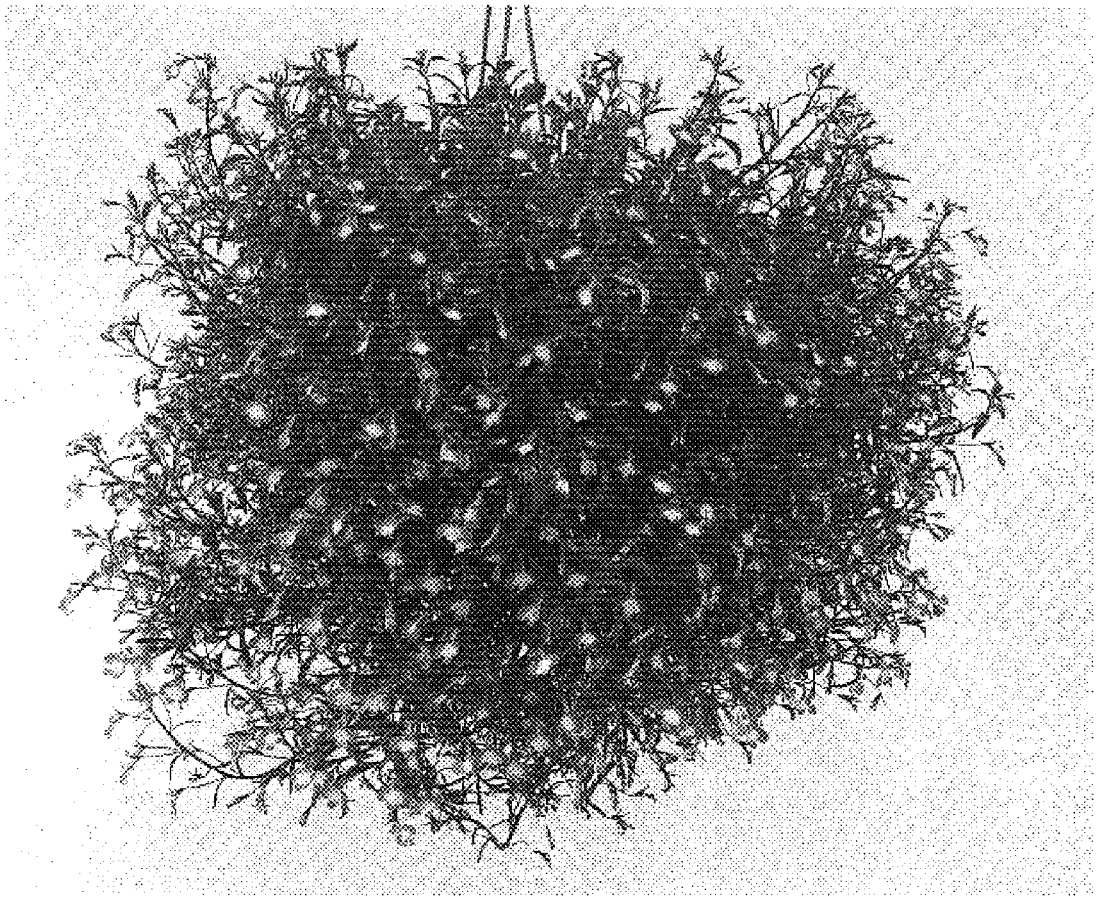

The accompanying photograph in FIG. 1 illustrates in full color a typical plant of 'DANANB6' grown in a greenhouse, in a 12 cm pot. Age of the plant photographed is approximately 90 days from a rooted cutting.

Figure 2:
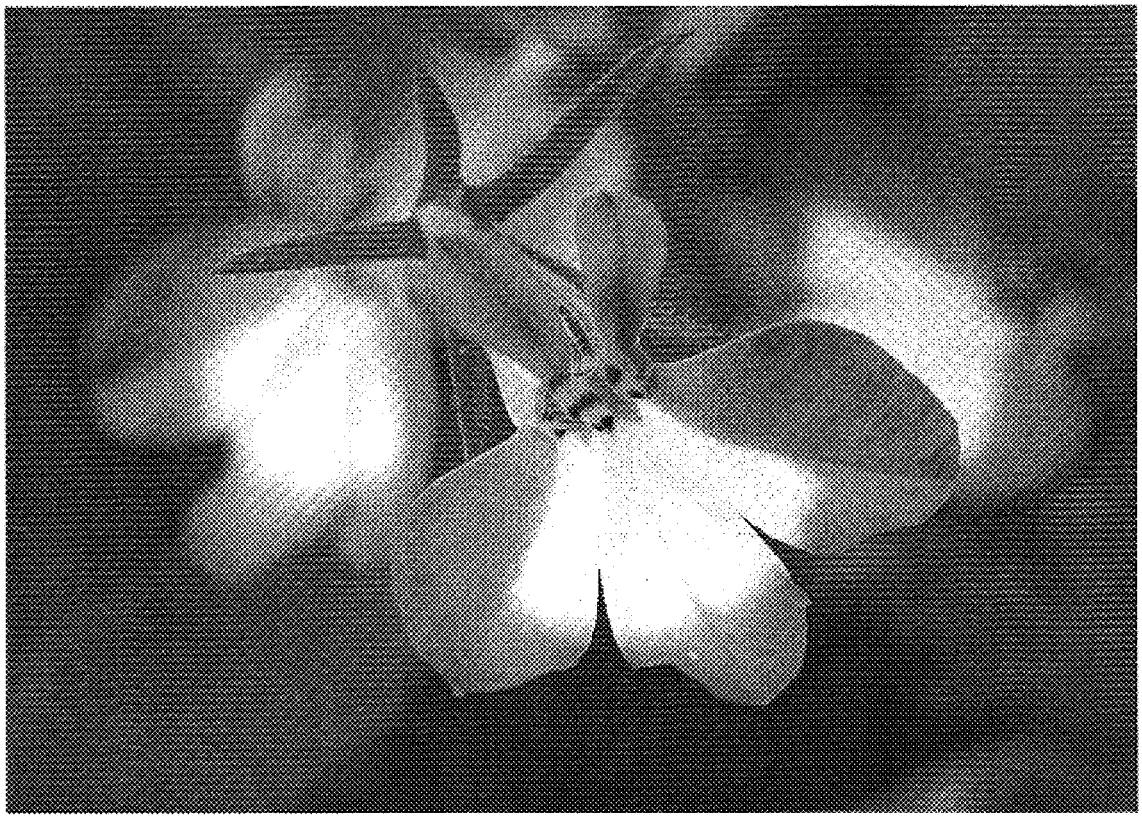

FIG. 2 illustrates in full color a close up of a typical bloom of 'DANANB6.'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANANB6' plants grown in a greenhouse in Moshav Mishmar Hashiva, Israel. The growing temperature ranged from 20° C. to 28° C. The greenhouse is un-shaded, giving bright, normal sunlight conditions. Measurements and numerical values represent averages of typical plant types.

Botanical classification: *Lobelia erinus* cultivar 'DANANB6.'

PROPAGATION

Time to initiate roots: About 5 days at approximately 15–30° C.
Root description: Fine, densely fibrous.
Time to produce a rooted cutting: About 15 days at 15–30° C.

PLANT

Growth habit: Trailing.
Pot size of plant described: 13 cm.
Height:
*To top of flowers.*—Approximately 27 cm.
Plant spread: Approximately 40 cm.
Growth rate: Rapid.
Branching characteristics: Free-branching.
Length of primary branches: Approximately 30 cm.
Length of secondary branches: Approximately 13 cm.
Diameter of primary branches: Approximately 0.4 cm
Quantity of primary and secondary branches: About 50.
Color of primary branches: Near RHS Green 137 B.
Texture: Pubescent
Internode length: Approximately 3 cm.
Age of plant described: Approximately 60 days from a rooted cutting.

FOLIAGE

Arrangement: Alternate.
Basal leaves:
*Size.*—Length: About 5 cm. Width: About 2 cm. Shape of leaf: Obovate. Shape of apex: Obtuse. Shape of base: Cuneate. Texture: Glabrous. Aspect: 90 degrees. Margin type: Serrate.
Midplant leaves:
*Size.*—Length: About 4.5 cm. Width: About 8 mm. Shape of leaf: Ligulate Shape of apex: Abruptly acute. Shape of base: Acuminate. Texture: Glabrous. Aspect: 45 to 90 degrees. Margin type: Serrate.
*Apical leaves.*—Size: Length: about 2.5 cm. Width: about 0.3 cm. Shape of leaf: Ligulate. Shape of apex: Acute. Shape of base: Cuneate. Texture: Glabrous. Aspect: 45 degrees. Margin type: Entire.
*Color.*—Young leaves: Upper surface: RHS Green 137C. Lower surface: RHS Green 137D. Mature leaves: Upper surface: RHS Green 137C. Lower surface: RHS Green 137D.
*Petiole.*—None.
*Veins.*—Venation pattern: Palmate. Color: Upper surface: RHS Green 137A. Lower surface: RHS Green 137B.

FLOWER

Natural flowering season: Flowering occurs continuously during growing season from spring until fall under Israeli climatic conditions.
Beginning flowering: Flowering begins approximately 3 weeks after planting a rooted cutting.
Flower type and habit: Flowers arranged singly at lateral apices.
Number of flowers per plant: Approximately 50.
Fragrance: None.
Longevity: Depending on weather conditions, 7–14 days for a single flower.
Flower size:
*Tube length.*—1 cm.
*Diameter.*—Distal end: 0.6 cm. Proximal end: 0.4 cm.
Flower shape and petal arrangement: Tubular with three larger lower petals and two upright petals.
Bud:
*Stage of development when described.*—(about 4 days prior to opening):
*Shape.*—Spatulate.
*Diameter.*—About 0.2 cm.
*Length.*—About 1.2 cm.
*Color.*—Near RHS Yellow-Green 149B.
Petals:
*Arrangement.*—Single whorl of five petals, not fused; three larger lower petals, two smaller upper petals.
*Quantity.*—3 larger lower petals and 2 smaller upper petals.
*Length.*—Lower petals: About 1.2 cm. Upper petals: About 0.6 cm.
*Width.*—Lower petals: 0.7 cm. Upper petals: 0.2 cm.
*Shape.*—Lower petals: Broadly oblong. Upper petals: Oblanceolate.
*Apex.*—Cuspidate.
*Base.*—Cuneate.
*Margin.*—Entire.
*Texture.*—Smooth.
*Color.*—When opening: RHS Blue 99D. Fully opened: RHS Blue 99D on the outside with white color on the inside of the petals.
*Throat.*—Veination: RHS White N999D. Spots: RHS Blue 99B.
*Tube.*—Veination: RHS Yellow 4A.
Sepals:
*Arrangement.*—Single whorl of five sepals, star-shaped calyx.
*Length.*—About 6.5 mm.
*Shape.*—Apiculate.
*Apex.*—Acute.
*Margin.*—Entire.
*Texture.*—Upper and lower surfaces: Pubescent.
*Color.*—Upper surface: 147A Lower surface: Yellow-Green 147A.
Peduncles:
*Length.*—About 3.5 cm.
*Diameter.*—About 0.7 mm.
*Color.*—147A.
*Texture.*—Sparsely pubescent to glabrous.
*Orientation.*—Angled.
*Strength.*—Wiry, flexible.

REPRODUCTIVE ORGANS

Stamens:
*Number (per flower).*—5 fused.
*Filament length.*—About 0.7 cm.
*Anthers.*—Shape: Ellipsoid. Length: About 0.4 cm. Diameter: About 0.2 cm. Color: RHS Violet-Blue 95B.

Pollen:

*Color.*—RHS Greyed-Yellow 160A.

*Amount.*—Moderate.

Pistils:

*Quantity per flower.*—1.

*Length.*—About 0.8 cm

*Styles.*—Length: About 0.5 cm. Color: Yellow-Green 146D.

*Stigma.*—Shape: Obovate. Color: Purple N79A. Ovary color: Yellow-Green 147B. Texture: Pubescent.

OTHER CHARACTERISTICS

Disease resistance: Neither resistance nor susceptibility observed.

Temperature tolerance: Tolerant to low temperature of about 2° C.

Seed and fruit production: Not observed and not commercially important.

What is claimed is:

1. A new and distinct cultivar of *Lobelia* plant named 'DANANB6' as herein illustrated and described.

* * * * *